United States Patent
Olson et al.

[11] Patent Number: 5,882,319
[45] Date of Patent: Mar. 16, 1999

[54] LAVAGE INSTRUMENT

[75] Inventors: Daniel H. Olson, Louisville; Michael J. Laco, Sherrodsville; Mark R. Rufener, Dover, all of Ohio

[73] Assignee: Bristol-Myers Squibb Company

[21] Appl. No.: 704,482

[22] Filed: Aug. 21, 1996

Related U.S. Application Data

[63] Continuation-in-part of Ser. No. 602,231, Feb. 16, 1996.

[51] Int. Cl.⁶ .................................................. A61H 9/00
[52] U.S. Cl. ........................ 601/161; 601/160; 601/155; 601/169
[58] Field of Search ................................ 601/154, 155, 601/159, 160, 161, 169

[56] References Cited

U.S. PATENT DOCUMENTS

| | | | |
|---|---|---|---|
| 615,019 | 11/1898 | Hershaw | 74/57 |
| 724,338 | 3/1903 | Sedivy | 74/57 |
| 1,005,690 | 10/1911 | Carlson | 74/57 |
| 1,122,376 | 12/1914 | Farmer | 74/57 |
| 1,232,202 | 7/1917 | Brown | 74/57 |
| 1,723,100 | 8/1929 | Voorhees | 74/57 |
| 1,734,649 | 11/1929 | Shull | 74/57 |
| 2,193,394 | 3/1940 | Deckert, Jr. | 74/57 |
| 2,245,457 | 6/1941 | Brassell | 74/57 |
| 2,296,164 | 9/1942 | Humphrey | 74/57 |
| 2,389,918 | 11/1945 | MacGill | 230/58 |
| 2,470,888 | 5/1949 | Degner | 74/57 |
| 2,705,592 | 4/1955 | Reiser | 230/188 |
| 3,227,158 | 1/1966 | Mattingly | 128/66 |
| 3,299,720 | 1/1967 | Schudalla, Sr. et al. | 74/57 |
| 3,696,809 | 10/1972 | Moret | 128/66 |
| 3,811,432 | 5/1974 | Moret | 128/66 |
| 4,145,166 | 3/1979 | Justice | 417/519 |
| 4,282,867 | 8/1981 | Du Toit | 128/66 |
| 4,315,741 | 2/1982 | Reichl | 433/82 |
| 4,655,197 | 4/1987 | Atkinson | 128/66 |
| 5,246,367 | 9/1993 | Ito et al. | 433/80 |
| 5,470,305 | 11/1995 | Arnett et al. | 601/161 |
| 5,542,909 | 8/1996 | Camp | 601/160 |

FOREIGN PATENT DOCUMENTS

| | | | |
|---|---|---|---|
| 0 029 636 A1 | 6/1981 | European Pat. Off. | A61H 13/00 |
| 2 262 890 | 7/1993 | United Kingdom | A61C 17/028 |

*Primary Examiner*—Robert A. Hafer
*Assistant Examiner*—Benjamin K. Koo
*Attorney, Agent, or Firm*—Todd A. Dawson

[57] ABSTRACT

The invention is directed to a self-powered lavage instrument used with an external fluid source for debridement of soft tissue. A housing includes at least two housing parts which are selectively attachable to and detachable from each other. A fluid nozzle is defined by or connected with the housing. A pump assembly is removably installed within the housing, and includes a case carrying an electric motor, a fluid pump and a plurality of power cells. The fluid pump is connected with the fluid nozzle and connectable with the external fluid source. The pump assembly further includes a plurality of clips, with each clip frictionally engaging and thereby electrically interconnecting two of the power cells.

10 Claims, 8 Drawing Sheets

LAVAGE INSTRUMENT

CROSS REFERENCE TO RELATED APPLICATIONS

This is a continuation-in-part of U.S. patent application Ser. No. 08/602,231, entitled "Lavage Instrument", filed Feb. 16, 1996.

BACKGROUND OF THE INVENTION

1. Field of the invention

The present invention relates to a lavage instrument, and, more particularly, to a hand held, battery powered lavage instrument for the debridement of soft tissue.

2. Description of the related art

Hand held lavage instruments are well known in the medical field. Lavage instruments are often used for the debridement of wounds and other body cavities. Typically, lavage instruments are connected to an external fluid source and an external vacuum pressure source. The vacuum source is used to evacuate the irrigation fluid and debris from the wound. Lavage instruments include a fluid pump and an electrical motor, which drives the fluid pump. Most lavage instrument assemblies include a housing which houses the electric motor and which is positioned remote from the hand held lavage instrument. Thus, the hand held lavage instrument primarily serves as a housing with two valves to control suction and irrigation. Recently, however, self-powered lavage instruments have been developed which use DC power cells to power the electrical motor which drives the internal fluid pump, thereby eliminating the need for the remotely located control housing. With such a known lavage instrument, the DC power cells are sealed within a hand held housing. Therefore, after the lavage procedure is finished, the entire hand held device is thrown away, including the batteries which could cause environmental problems.

SUMMARY OF THE INVENTION

The present invention provides a lavage instrument which includes a hand held housing formed in two parts and held together by a removable strap. A battery pack including a plurality of batteries is enclosed within the housing. After the procedure is over, but before the instrument is thrown away, the user can remove the strap, separate the housing, and remove the battery pack including the batteries. The batteries can be removed from the battery pack and used somewhere else or disposed of properly.

The invention comprises, in one form thereof, a self-powered lavage instrument used with an external fluid source for debridement of soft tissue. A housing includes at least two housing parts which are selectively attachable to and detachable from each other. A fluid nozzle is defined by or connected with the housing. A fluid pump enclosed within the housing is connected with the fluid nozzle and connectable with the external fluid source. At least one power cell is enclosed within the housing and connected to the fluid pump. The at least one power cell may be removed from the housing upon detachment between the housing parts.

The invention comprises, in another form thereof, a self-powered lavage instrument used with an external fluid source for debridement of soft tissue. A housing includes at least two housing parts which are selectively attachable to and detachable from each other. A fluid nozzle is defined by or connected with the housing. A pump assembly is removably installed within the housing, and includes a case carrying an electric motor, a fluid pump and a plurality of power cells. The fluid pump is connected with the fluid nozzle and connectable with the external fluid source. The pump assembly further includes a plurality of clips, with each clip frictionally engaging and thereby electrically interconnecting two of the power cells.

An advantage of the present invention is that the batteries disposed within the housing may be removed from the housing after use of the lavage instrument, and subsequently reused or recycled.

Another advantage is that a pump assembly includes the battery pack with the plurality of batteries integral therewith, with the entire pump assembly being removable from the housing after use of the lavage instrument.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Referring now to the drawings and particularly to FIGS. 1–4, there is shown a lavage instrument 10 of the present invention which includes a contoured outer housing 20. Housing 20 has a cylindrical base 22, a pistol grip shaped neck 24 and a curved head 26. A fluid nozzle 12 and a suction nozzle 13 protrude from the face 27 of housing head 26.

Figures 1, 1A:
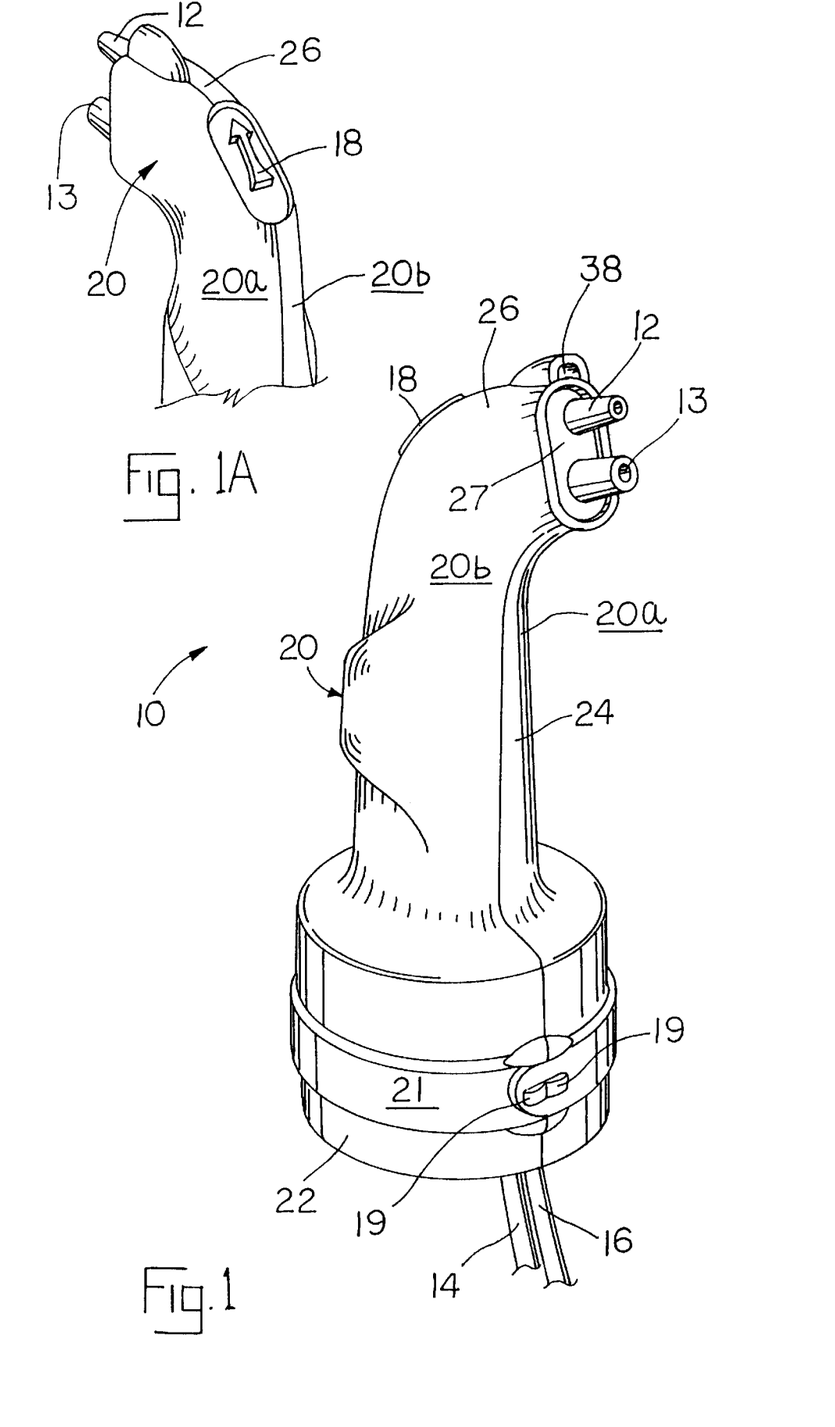
FIG. 1 is a frontal, perspective view of an embodiment of a lavage instrument of the present invention.
FIG. 1A is a fragmentary, perspective view of the top of the lavage instrument shown in FIG. 1.
Figure 2:
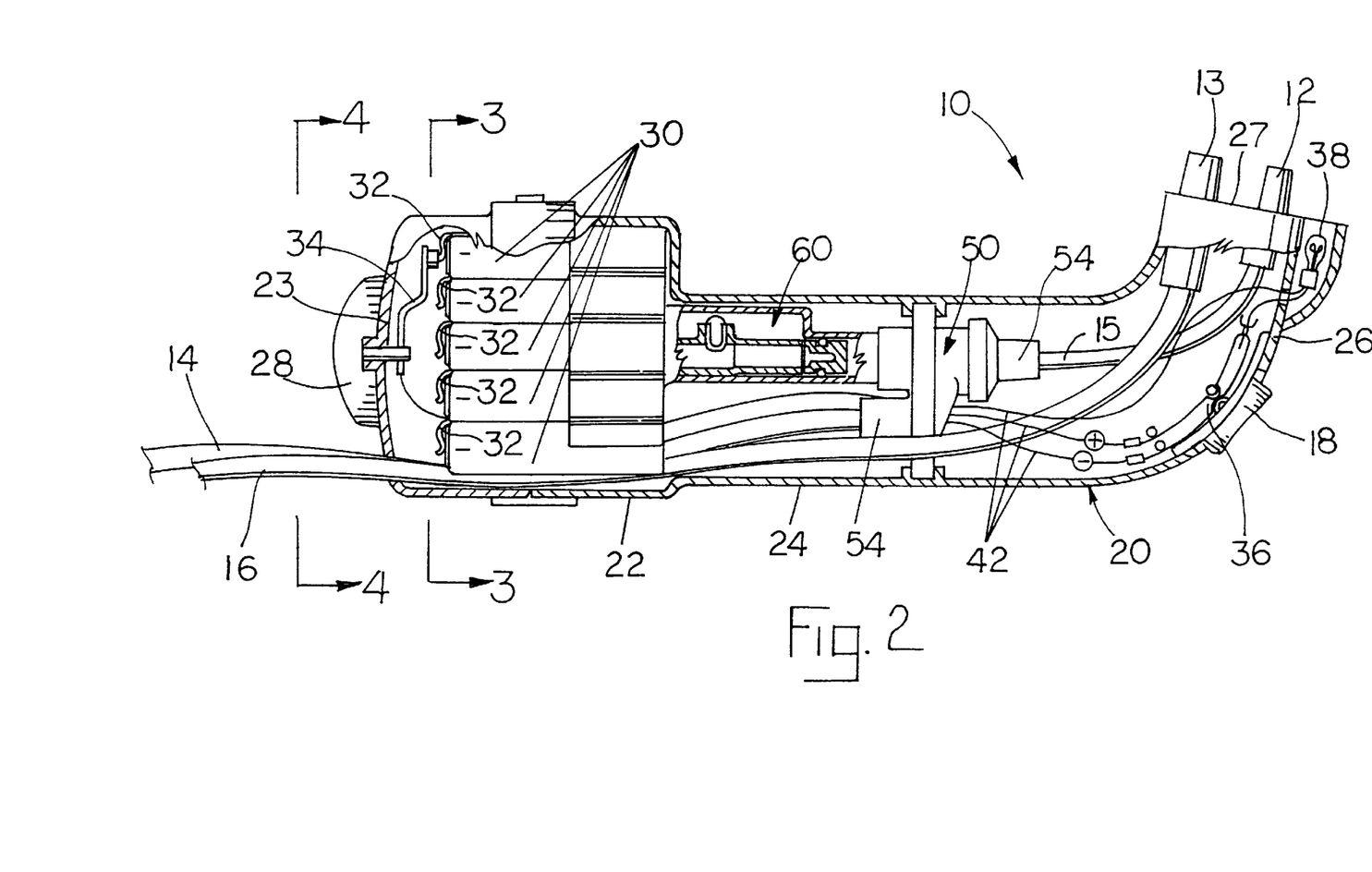
FIG. 2 is a side sectional view of the lavage instrument shown in FIGS. 1 and 2.

Housing 20 encloses the internal components of instrument 10 including: eight DC power cells or batteries 30, contactor arm 34, on/off switch 36, light fixture 38, electric motor 40 and an integrally connected fluid reservoir 50 and fluid pump 60. Housing 20 is formed in two parts, 20a and 20b, which are held together by a resilient strap 21. Each end of strap 21 has a hole (not numbered) therethrough for connection of strap 21 to nibs 19 extending from housing parts 20a and 20b. Strap 21 may be removed and housing 20 opened to remove batteries 30 for reuse or proper disposal after the lavage instrument is used. One of housing parts 20a, 20b may include a lip or projection (not shown) near head 26 for mating with an associated opening or flange (not shown) formed in the other housing part 20a, 20b.

Figure 3:
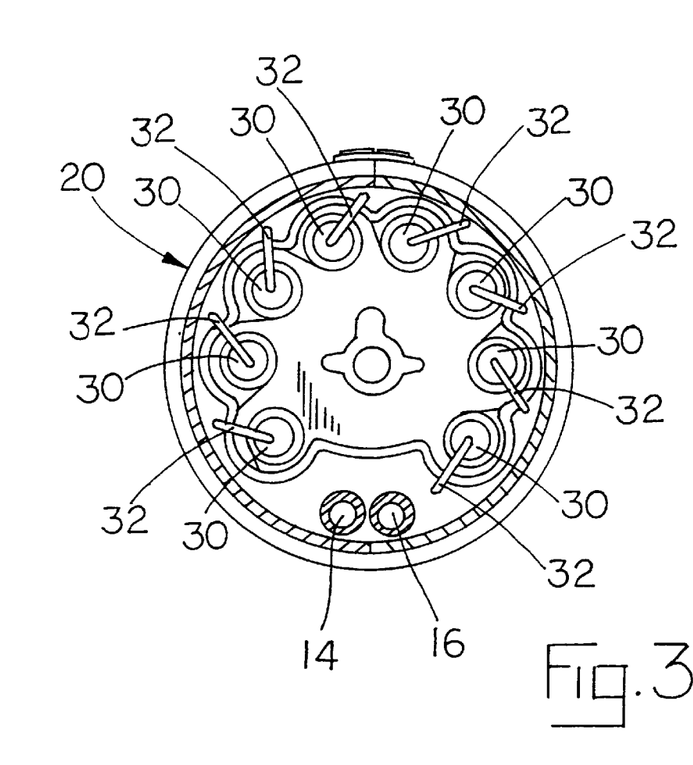
FIG. 3 is a sectional view taken along line 3—3 in FIG. 2.

As shown in FIGS. 2 and 3, power cells 30 are arranged within housing base 22 around motor 40 with their negative poles facing the bottom cap 23 of housing base 22. Motor 40 is of conventional design and any suitable direct current electric motor, which turns a drive shaft, may be employed. Preferably, motor 40 is a separate component from fluid pump 60; however, the motor can be incorporated into the design of fluid pump 60 if desired. In the embodiment shown, motor 40, fluid reservoir 50, fluid pump 60, and power cells 30 define a pump assembly 46, described in more detail below.

Power cells 30 are connected in series by eight battery terminals or clips 32. Each battery terminal 32 includes a conductive wire and electrically connects the positive pole of one power cell to the negative pole of an adjacent power cell in a series arrangement. A wiring harness 42 connects each battery terminal 32 to motor 40, an on/off contactor switch 36, and a light fixture 38. Instrument 10 includes light fixture 38 for illuminating the wound or cavity during debridement. On/off switch 36 is actuated by an on/off pad 18, which protrudes from housing head 26. Depression of on/off pad 18 closes the contacts of on/off switch 36 to actuate instrument 10.

Figure 4:
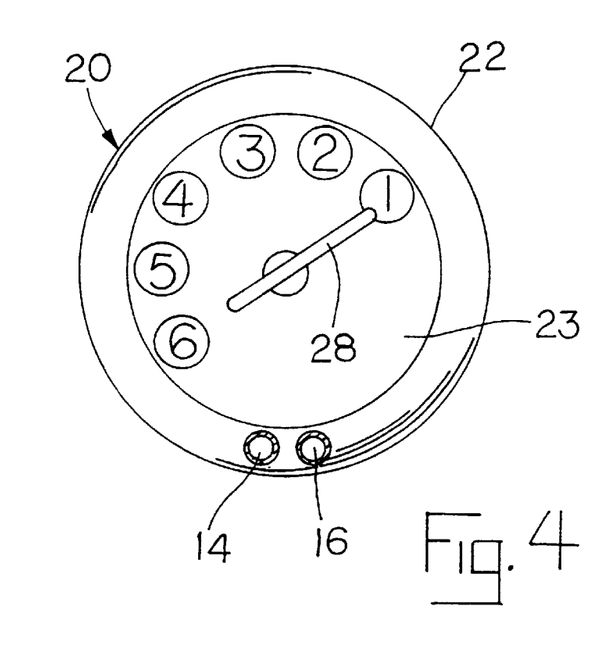
FIG. 4 is a sectional view taken along line 4—4 in FIG. 2.
Figure 5:
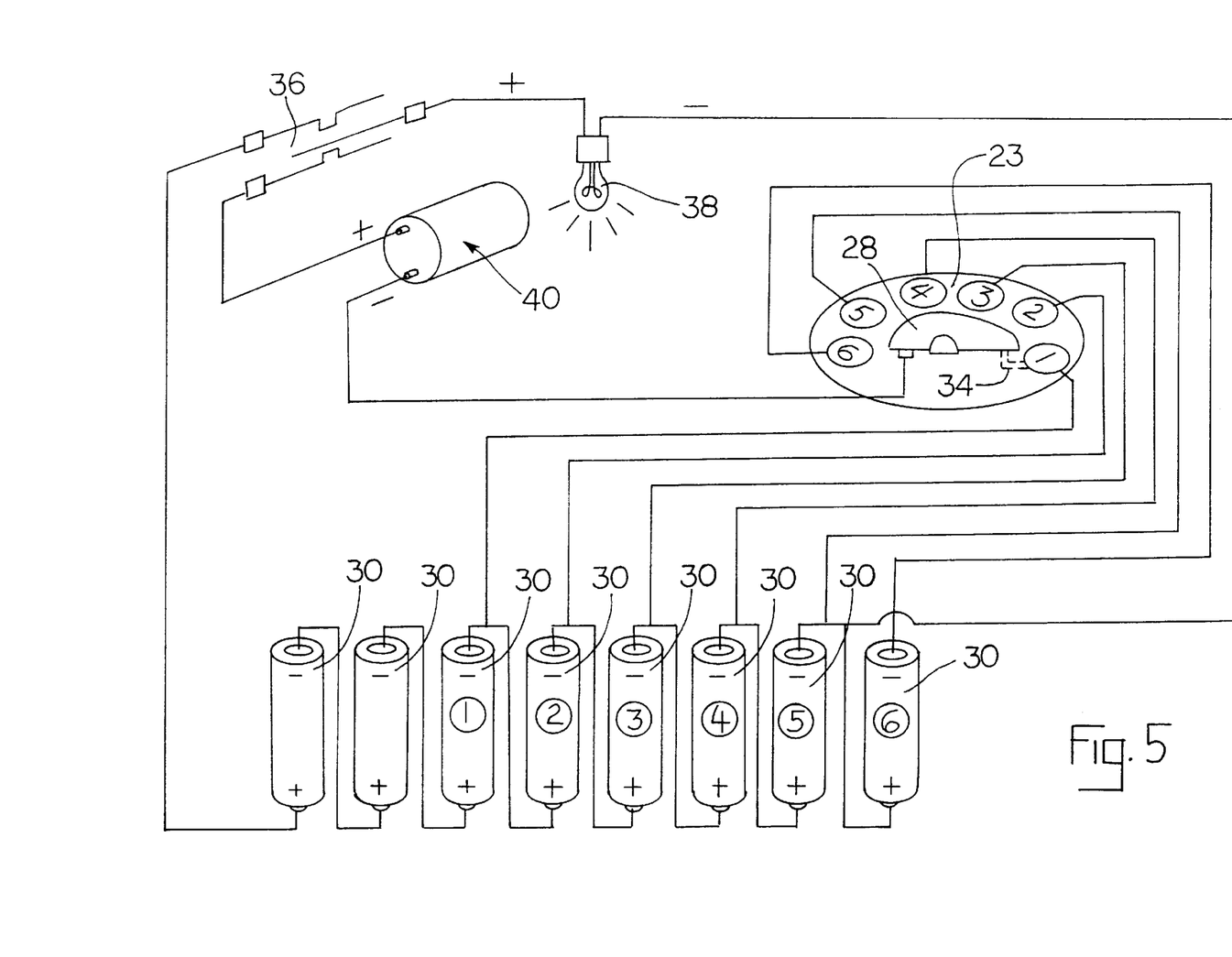
FIG. 5 is a simplified schematic of the electrical wiring for the lavage instrument shown in FIGS. 1–4.

As shown in FIGS. 2, 4 and 5, a rotatable speed selection knob 28 mounted to bottom cap 23 of housing base 22 turns an elongated contactor arm 34. Selection knob 28 can be positioned at one of several discrete speed settings. At each position or speed setting of selection knob 28, contactor arm 34 engages a different battery terminal 32. The electrical connection between contactor arm 34 and each battery terminal 32 provides a discrete voltage output to motor 40 at each speed setting. The different voltage outputs produce different motor speeds and therefore, different fluid flow rates. As shown, two of power cells 30 provide the minimum voltage required to drive motor 40. The six remaining power cells 30 provide additional incremental voltage to drive motor 40. Further, the arrangement of the power cells 30 provides an arrangement wherein extra batteries 30 are available at lower speed settings. For example, if the user is satisfied with the speed of the unit with only 4 batteries being used (i.e. position 2) as the power cells are used up and the motor begins to slow, additional power cells 30 can be switched into the circuit by progressively rotating the selection knob 28 to the next position. Eight power cells 30 are shown although any number of power cells 30 may be incorporated into the design of the instrument.

As shown in FIG. 2, fluid reservoir 50 and fluid pump 60 are supported within housing neck 24. Fluid reservoir 50 includes an inlet port 52 and an outlet port 54. An external fluid line 16, is connected to inlet port 52 and passes through the bottom of housing base 22. An internal fluid line 15 connects outlet port 54 to fluid nozzle 12. A suction line 14, which is connected to suction nozzle 13, passes through housing 12 and exits through the bottom of housing base 22.

Referring now to FIGS. 6–13, pump assembly 46 will be described in greater detail. As indicated above, pump assembly 46 generally includes a motor 40, fluid reservoir 50, fluid pump 60 and power cells 30. Pump assembly 46 is removably installed within housing parts 20a, 20b of housing 20 during operation of lavage instrument 10. Pump assembly 46 includes a case 64 which carries electric motor 40, fluid pump 60 and power cells 30. Additionally, pump assembly 46 also includes the plurality of battery terminals or clips 32 which electrically interconnect adjacent power cells 30. Case 64, power cells 30 and clips 32 define a battery pack (not numbered) which is enclosed within housing 20 of lavage instrument 10.

Figure 6:
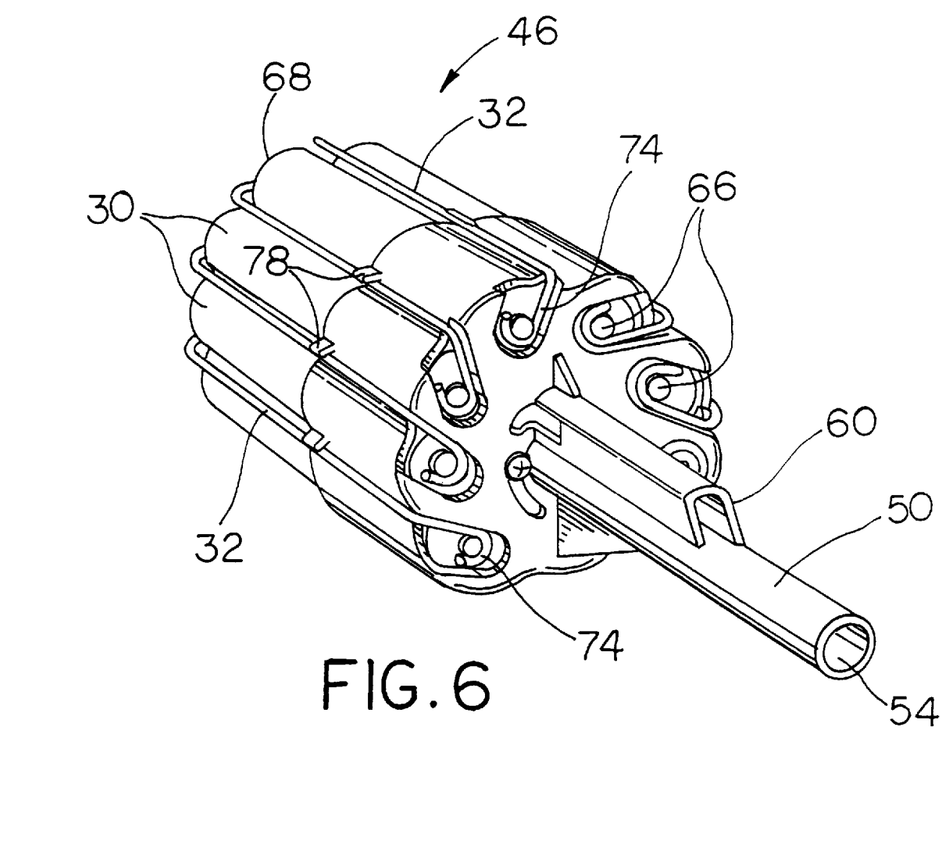
FIG. 6 is a perspective view of the pump assembly shown in FIGS. 2 and 3, when removed from the housing.
Figures 7, 8:
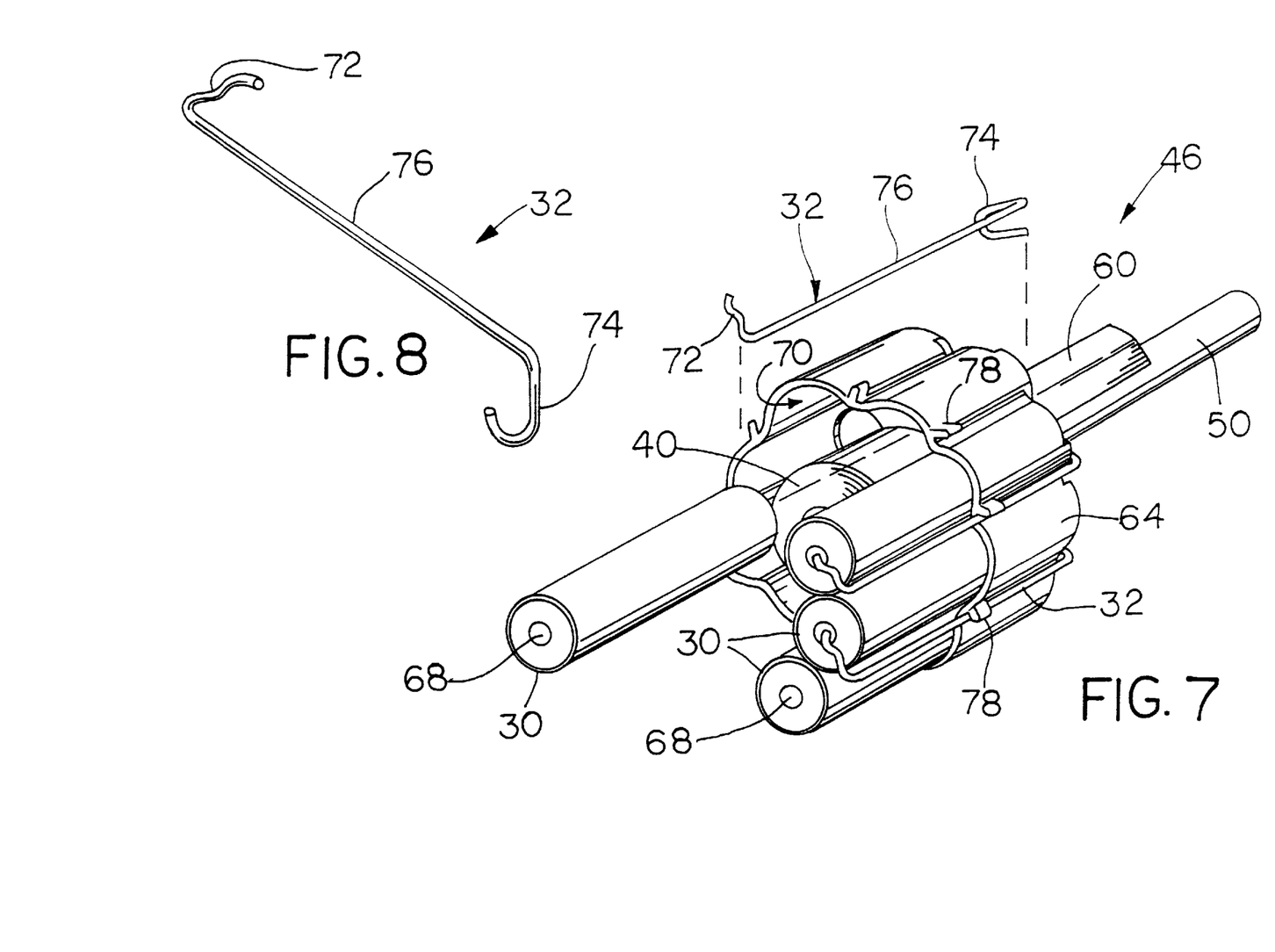
FIG. 7 is another perspective view of the pump assembly, with one of the batteries and a wire clip removed.
FIG. 8 is another perspective view of the removed wire clip shown in FIG. 7.
Figure 9:
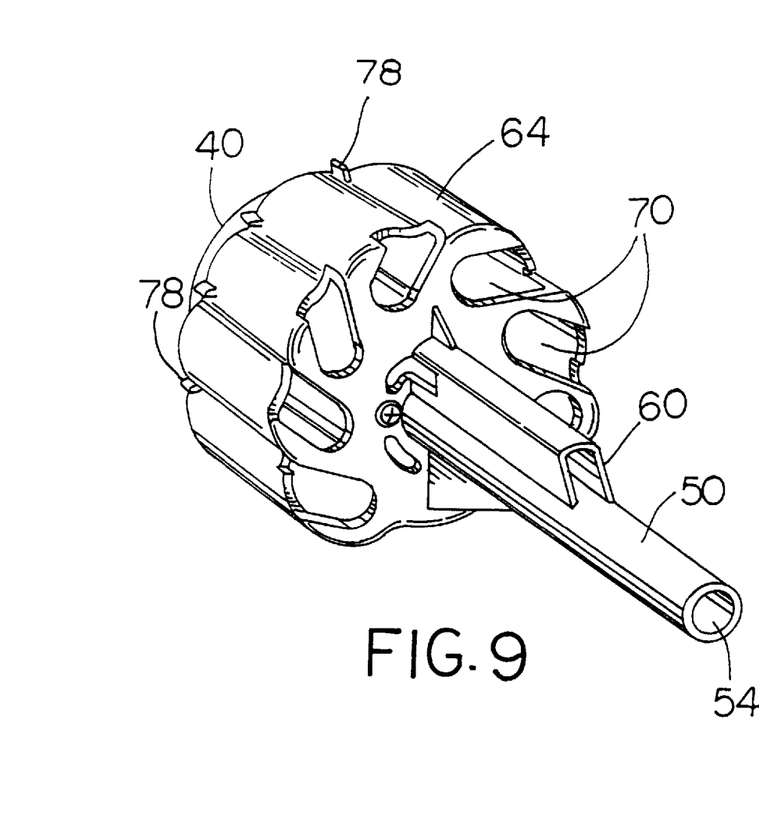
FIGS. 9 and 10 are perspective views of the pump assembly shown in FIGS. 6 and 7, with the batteries and wire clips removed.
Figure 10:
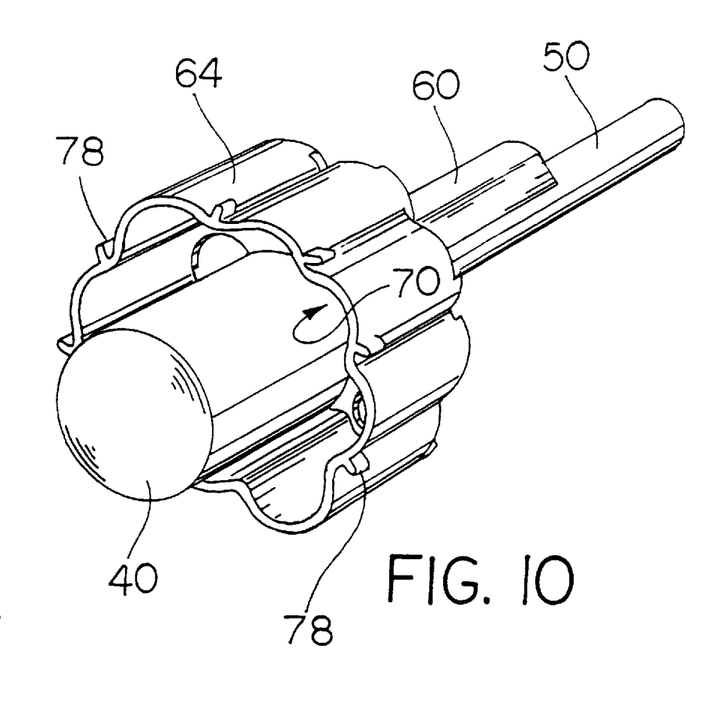
Figures 11, 12, 13:
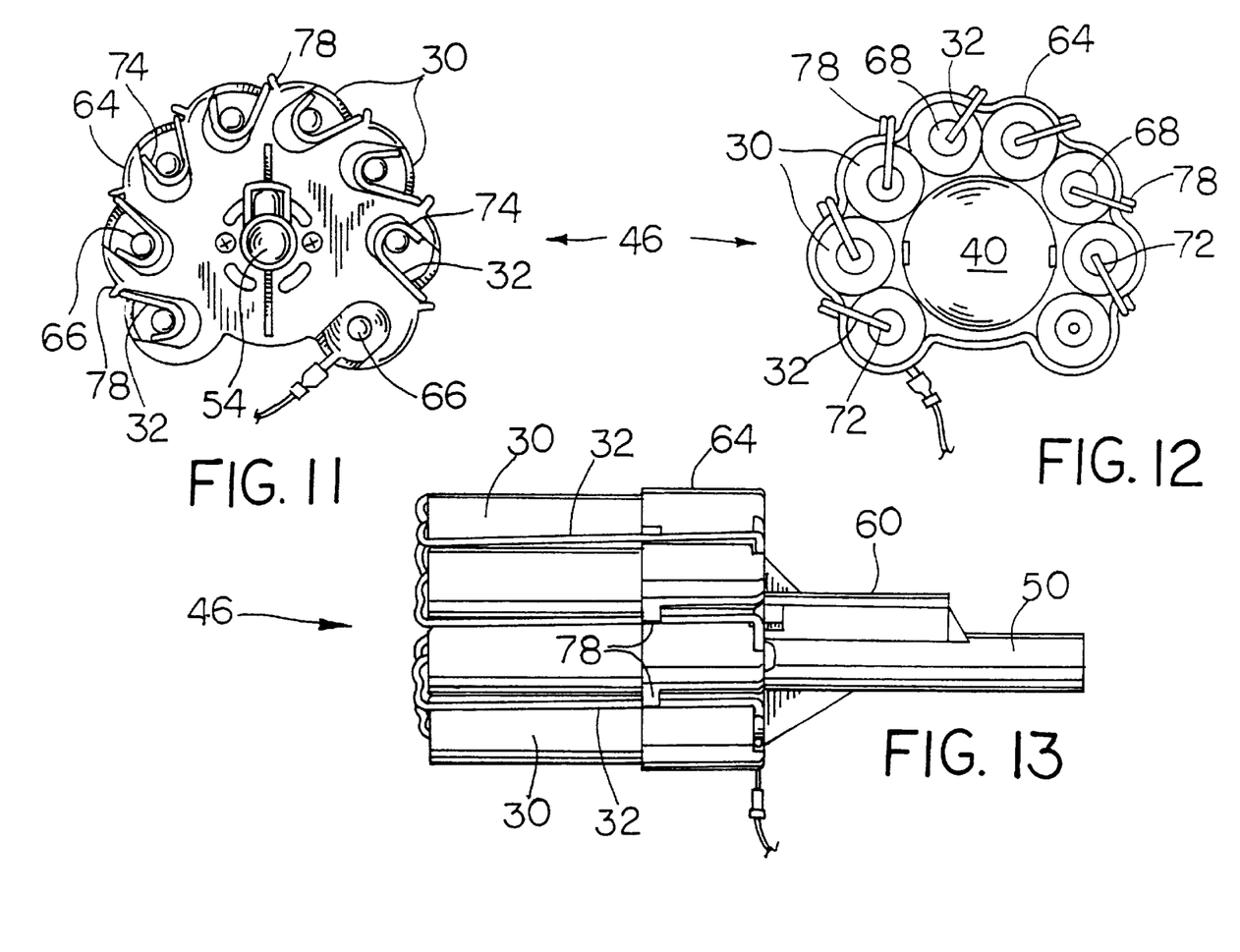
FIG. 11 is an end view of the pump assembly with the batteries and wire clips installed, viewed from the outlet end of the pump.
FIG. 12 is an end view of the pump assembly with the batteries and wire clips installed, viewed from the opposing end of the pump.
FIG. 13 is a side view of the pump assembly shown in FIGS. 11 and 12.

The plurality of power cells 30 are in the form of a plurality of DC batteries 30, as indicated above. Each battery 30 has a positive pole 66 and a negative pole 68 at opposing ends thereof (FIGS. 6 and 7). The plurality of batteries 30 are disposed in parallel, side-by-side relationship to each other such that positive poles 66 are disposed adjacent to each other (i.e., all facing the fluid pump 60), and the negative poles 68 are disposed adjacent to each other (i.e., all facing the opposing end of pump assembly 46). The plurality of batteries 30 are disposed in a plurality of respective openings 70 (FIGS. 9 and 10) defined by and between case 64 and motor 40. The plurality of batteries 30 thus at least partially surround electric motor 40 carried by case 64.

Battery terminals or clips 32 provide the dual functionality of both interconnecting power cells 30 in a series arrangement and holding power cells 30 within case 64. More particularly, and as may best be seen in FIGS. 6 and 7, clips 32 connect a positive pole 66 of a particular battery 30 to a negative pole 68 of an adjacent battery 30. Each clip 32 is formed from a substantially resilient material and includes opposing ends 72, 74 which extend substantially perpendicular to a longitudinal axis defined by a center portion 76 (FIG. 8). Ends 72, 74 frictionally engage and thereby electrically interconnect the positive pole of one battery 30 to the negative pole of an adjacent battery 30. A plurality of projections 78 extending from case 64 hold the respective clips 32 in a relatively stationary position when clips 32 are installed on pump assembly 46.

During use, pump assembly 46 is enclosed within housing 20 of lavage instrument 10 and provides a self-powered, compact unit to pump fluid from lavage instrument 10. After lavage instrument 10 is used and debridement of the soft tissue is finished, strap 21 is removed from the exterior of housing 20 and housing parts 20a, 20b are detached from each other to expose pump assembly 46 disposed therein. A user grasps pump assembly 46 and removes it as an entire unit from lavage instrument 10. Clips 32 are pulled in a sideways direction (i.e., substantially perpendicular to the longitudinal axis of center portions 76) to remove them from pump assembly 46. Batteries 30 may then be slid in an axial direction from the respective openings 70 defined by case 64 to be reused or properly discarded.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A self-powered lavage instrument used with an external fluid source for debridement of soft tissue, said lavage instrument comprising:

a housing including at least two housing parts, said housing parts being selectively attachable to and detachable from each other;

a fluid nozzle being one of defined by and connected with said housing;

a fluid pump enclosed within said housing, said fluid pump connected with said fluid nozzle and connectable with the external fluid source; and at least one power cell enclosed within said housing and connected to said fluid pump;

wherein said at least one power cell may be removed from said housing upon detachment between said housing parts, further comprising a strap disposed around said at least two housing parts for providing said selective attachment and detachment therebetween and wherein at least one of said housing parts includes at least one nib extending from an exterior thereof, and wherein said strap includes opposing ends with a hole in each said end, said strap openings configured to receive an associated said nib therein.

2. The lavage instrument of claim 1, wherein said at least one power cell comprises a plurality of DC batteries.

3. The lavage instrument of claim 1, wherein said at least one power cell comprises a plurality of DC batteries, and further comprising a case enclosed within said housing and carrying said plurality of DC batteries, said case and said DC batteries defining a battery pack which is removable from said housing upon detachment between said housing parts.

4. A self-powered lavage instrument used with an external fluid source for debridement of soft tissue, said lavage instrument comprising:

a housing including at least two housing parts, said housing parts being selectively attachable to and detachable from each other;

a fluid nozzle being one of defined by and connected with said housing;

a fluid pump enclosed within said housing, said fluid pump having an outlet connected with said fluid nozzle and having an inlet connectable with the external fluid source; and a battery pack enclosed within said housing, said battery pack including a case carrying a plurality of power cells, said battery pack farther including a plurality of clips which electrically interconnect said power cells, further comprising a strap disposed around said at least two housing parts for providing said selective attachment and detachment therebetween and wherein at least one of said housing parts includes at least one nib extending from an exterior thereof, and wherein said strap includes opposing ends with a hole in each said end, said strap openings configured to receive an associated said nib therein.

5. The lavage instrument of claim 4, wherein said plurality of clips interconnect said power cells in series.

6. The lavage instrument of claim 4, wherein said clips provide a dual functionality of interconnecting said power cells in series and holding said power cells within said case.

7. The lavage instrument of claim 4, wherein said plurality of power cells comprise a plurality of DC batteries, each said battery having a positive pole and a negative pole at opposing ends thereof, said clips connecting a positive pole of one said battery to a negative pole of an adjacent said battery.

8. The lavage instrument of claim 7, wherein said plurality of batteries are disposed in parallel, side-by-side relationship to each other such that said positive poles are disposed adjacent to each other and said negative poles are disposed adjacent to each other.

9. The lavage instrument of claim 4, wherein said case also carries an electric motor, and wherein said plurality of power cells at least partially surround said electric motor.

10. The lavage instrument of claim 4, wherein said case defines a plurality of openings, said plurality of power cells being disposed within respective said openings.

* * * * *